United States Patent
Iwasaki et al.

[11] Patent Number: 5,100,920
[45] Date of Patent: Mar. 31, 1992

[54] MITICIDE

[75] Inventors: Tetsuji Iwasaki, Wakayama; Kazuhiko Kurita, Kainan, both of Japan

[73] Assignee: Kao Corporation, Tokyo, Japan

[21] Appl. No.: 897,690

[22] Filed: Aug. 1, 1986

[30] Foreign Application Priority Data

Mar. 18, 1985 [JP] Japan .................. 60-53590

[51] Int. Cl.$^5$ ............................ A01N 33/12
[52] U.S. Cl. .................... 514/642; 514/643
[58] Field of Search ............... 514/642, 643, 442, 517, 514/546, 636

[56] References Cited

U.S. PATENT DOCUMENTS

| | | | |
|---|---|---|---|
| 2,547,724 | 8/1951 | Sundholm | 514/442 |
| 3,054,678 | 9/1962 | Michener et al. | 514/642 |
| 3,730,702 | 5/1973 | Shay et al. | 514/642 |
| 4,017,635 | 8/1977 | Ishiguro | 514/517 |
| 4,201,786 | 5/1980 | Kaplan | 514/465 |
| 4,430,341 | 2/1984 | Kaplan | 514/255 |

FOREIGN PATENT DOCUMENTS 2625945 2/1977 Fed. Rep. of Germany.

*Primary Examiner*—Frederick E. Waddell
*Assistant Examiner*—Zohreh A. Fay
*Attorney, Agent, or Firm*—Flynn, Thiel, Boutell & Tanis

[57] ABSTRACT

A quaternary ammonium salt of the general formula (I):

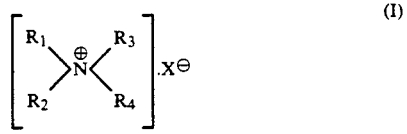

wherein $R_1$ and $R_2$ represent each

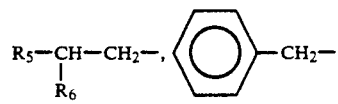

or an alkyl group having one to four carbon atoms provided that at least of them is

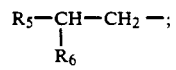

wherein $R_5$ represents an alkyl or alkenyl group having four to 22 carbon atoms, and $R_6$ represents an alkyl or alkenyl group having two to 20 carbon atoms; $R_3$ and $R_4$ represent each an alkyl group having one to four carbon atoms or $-CH_2CH_2OH$; and $X^\ominus$ represents a counter anion: is an effective miticide and causes no chemical damage to fruit trees and vegetables.

13 Claims, No Drawings

MITICIDE

This invention relates to a miticide. More particularly it relates to a miticide which is effective against chemical resistant mites and causes no chemical damage to fruit trees and vegetables.

PRIOR ART

Recently, chemical miticides have been widely applied to various crops including fruits and vegetables. Mites generally breed from early spring to autumn. However, recent extension of grass culture has brought about serious damage from mites even in winter. Application of a chemical miticide will restrict the density of mite growth for a period of as long as one month. However, this inhibitory effect is still insufficient from the viewpoint of the culturing period of crops. Therefore, miticides are repeatedly applied in general. The impartation of chemical resistance to mites can be prevented to a certain extent by avoiding repeated application of the same miticide. However, such an application is not operated with sufficient care at present.

The breeding power of mites is so vigorous that the chemical resistance of the mites has frequently become a problem even in the cases where various chemicals are alternately employed.

Similar to the cases of bactericides and herbicides, it requires approximately ten years to develop a chemical miticide. Therefore, impartation of chemical resistances is a serious problem for manufacturers.

On the other hand, agricultural machine oil is known as a chemical which imparts no resistance. However the concentration of the same wherein it is effective in exterminating mites without any damage to crops is very limited, which makes it practically unavailable for crops including vegetables.

DISCLOSURE OF INVENTION

Under these circumstances, we have attempted to develop a compound which is effective against chemical-resistant mites and causes no chemical damage to crops including fruit trees and vegetables and consequently completed the present invention.

Accordingly, the present invention provides a miticide comprising a quaternary ammonium salt of the general formula (I):

$$\left[ \begin{array}{c} R_1 \\ R_2 \end{array} \!\!\!\! \underset{\oplus}{N} \!\!\!\! \begin{array}{c} R_3 \\ R_4 \end{array} \right] . X^{\ominus} \qquad (I)$$

wherein $R_1$ and $R_2$ represent each $$R_5-\underset{R_6}{\underset{|}{CH}}-CH_2-\underset{}{\bigcirc}-CH_2$$

or an alkyl group having one to four carbon atoms provided that at least one of them represents $$R_5-\underset{R_6}{\underset{|}{CH}}-CH_2,$$

wherein $R_5$ represents an alkyl or alkenyl group having four to 22 carbon atoms; and $R_6$ represents an alkyl or alkenyl group having two to 20 carbon atoms; $R_3$ and $R_4$ represent each an alkyl group having one to four carbon atoms or $-CH_2CH_2OH$; and $X^-$ represents a counter anion.

Preferable examples of the counter anion X are Cl, Br or $CH_3SO_4$.

The present invention further provides a miticide solution containing said quaternary ammonium salt as an active ingredients, wherein the active compound is dissolved preferably in water at a concentration of 10 to 2000 ppm in general.

The miticide solution of the present invention may further contain conventional miticides.

The compound (I) according to the present invention may be prepared in a known manner. For example, it may be prepared by quaternizing a tertiary amine of the general formula (II) with a quaternizing agent such as methyl chloride, methyl bromide or dimethyl sulfate:

$$\begin{array}{c} R_1 \\ R_2 \end{array} \!\!\!\! N-R_3 \qquad (II)$$

wherein $R_1$, $R_2$ and $R_3$ are as defined in formula (I).

The tertiary amine of the formula (II) may be similarly prepared in a known manner. For example, it may be prepared by directly reacting an alcohol of the formula (III) with methylamine or dimethylamine:

$$R_5-\underset{R_6}{\underset{|}{CH}}-CH_2-OH \qquad (III)$$

wherein $R_5$ and $R_6$ are as defined in formula (I).

Among the compounds of the general formula (I) according to the present invention, those represented by the formula (IV) or (V):

$$\left[ CH_3\!\!-\!\!(CH_2)_{\overline{n}}\!-\!\underset{(CH_2)_{n-2}}{\underset{|}{CH}}\!-\!CH_2\!-\!\underset{CH_3}{\overset{CH_3}{\underset{|}{\overset{|}{N^{\oplus}}}}}\!-\!CH_3 \right] . X^{\ominus} \qquad (IV)$$

$$\underset{|}{\underset{CH_3}{|}}$$

wherein n represents an integer of 3 to 21 and X represents Cl, Br or $CH_3SO_4$; and $$\left[ CH_3\!\!-\!\!(CH_2)_{\overline{n}}\!-\!\underset{(CH_2)_{n-2}}{\underset{|}{CH}}\!-\!CH_2\!-\!\underset{CH_2}{\overset{CH_3}{\underset{|}{\overset{|}{N^{\oplus}}}}}\!-\!CH_3 \right] . X^{\ominus} \qquad (V)$$

wherein n and m represent each an integer of 3 to 21 and X represents Cl, Br or $CH_3SO_4$; are particularly preferable.

The miticide of the present invention may be applied on crops including vegetables and fruit trees in the form of an aqueous solution or an aqueous dispersion.

The miticide of the present invention may be applied at a concentration of 10 ppm or above, preferably 100 to 2000 ppm. Within the range as defined above, it exerts an effect of exterminating mites which are parasitic on broadleaf crops such as soybean and cotton, true grasses such as rice and wheat, vegetables such as cucumber and egg plant and fruit trees such as apple, pear and orange trees without causing any chemical damage to the crops.

The miticide of the present invention is effective on various parasitic mites such as Tarsonemidae, Pyemotidae, Eupodidae, Tydeidae, Tetranychidae and Tenuipalpidae.

The compound of the present invention exhibits a remarkable synergistic effect when using together with conventional chemical miticides. The effect obtained by simultaneously using these miticides is particularly remarkable on chemical-resistant mites (cf. Example 2).

The miticide of the present invention is usually used in a weight ratio of 0.1/1 to 20/1 based on the chemical miticide components.

BEST MODE FOR CARRYING OUT THE INVENTION

The following Examples will be given in order to illustrate the miticidal activity of the compound of the present invention and the synergistic effect obtained by applying it together with commercially available chemical miticides.

EXAMPLE 1

30 female imagoes of *Tetranychus urtiae* were inoculated on a kidney bean leaf piece (3 cm×3 cm) and allowed to stand at 26° C. for 12 hours. After confirming the number of surviving mites, 0.2 ml portions of the miticide of the present invention, a comparison compound and commercially available miticides, each at concentrations of 100 and 1000 ppm, were applied on the leaf discs. After allowing them to stand at 26° C. for 24 hours, dead mites on each disc were counted and the miticidal ratio to the untreated lot (treated with water alone) was determined. This procedure was repeated ten times and the mortality was represented on the average. Table 1 shows the result.

TABLE 1

| Compound of invention No. | Structure of compound of invention | Miticidal ratio Concentration of chemical | |
|---|---|---|---|
| | | 100 ppm | 1000 ppm |
| 1 | $\left[ CH_3(CH_2)_6CHCH_2-\underset{\underset{CH_3}{\mid}}{\overset{\overset{CH_3}{\mid}}{N}}-CH_3 \atop \underset{CH_3}{\mid}(CH_2)_4 \right] Cl^-$ | 33 | 69 |
| 2 | $\left[ CH_3(CH_2)_{10}CHCH_2-\underset{\underset{CH_3}{\mid}}{\overset{\overset{CH_3}{\mid}}{N}}-CH_3 \atop \underset{CH_3}{\mid}(CH_2)_8 \right] Cl^-$ | 35 | 75 |
| 3 | $\left[ CH_3(CH_2)_{12}CHCH_2-\underset{\underset{CH_3}{\mid}}{\overset{\overset{CH_3}{\mid}}{N}}-CH_3 \atop \underset{CH_3}{\mid}(CH_2)_{10} \right] Cl^-$ | 39 | 80 |
| 4 | $\left[ CH_3(CH_2)_{14}CHCH_2-\underset{\underset{CH_3}{\mid}}{\overset{\overset{CH_3}{\mid}}{N}}-CH_3 \atop \underset{CH_3}{\mid}(CH_2)_{12} \right] Cl^-$ | 41 | 84 |
| 5 | $\left[ CH_3(CH_2)_{16}CHCH_2-\underset{\underset{CH_3}{\mid}}{\overset{\overset{CH_3}{\mid}}{N}}-CH_3 \atop \underset{CH_3}{\mid}(CH_2)_{14} \right] Cl^-$ | 49 | 95 |

TABLE 1-continued

| Compound of invention No. | Structure of compound of invention | Miticidal ratio Concentration of chemical | |
|---|---|---|---|
| | | 100 ppm | 1000 ppm |
| 6 | [CH₃(CH₂)₁₈CHCH₂—N(CH₃)₃ ; (CH₂)₁₆CH₃] Cl⁻ | 56 | 95 |
| 7 | [CH₃(CH₂)₈CH=CH(CH₂)₄CHCH₂N(CH₃)₂ ; (CH₂)₄CH₃ ; CH=CH(CH₂)₆CH₃] Cl⁻ | 59 | 96 |
| 8 | [CH₃(CH₂)₁₀CH=CH(CH₂)₄CHCH₂N(CH₃)₂ ; (CH₂)₄CH₃ ; CH=CH(CH₂)₈CH₃] Br⁻ | 62 | 96 |
| 9 | [(CH₃(CH₂)₈CHCH₂—(CH₂)₄CH₃)₂N(CH₃)₂ with second chain CH₃(CH₂)₈CHCH₂(CH₂)₆CH₃] CH₃SO₄⁻ | 54 | 95 |
| 10 | [(CH₃(CH₂)₁₈CHCH₂—(CH₂)₁₆CH₃)₂N(CH₃)₂] Cl⁻ | 56 | 95 |
| Comparison 1 | [CH₃(CH₂)₁₁—N(CH₃)₃] Cl⁻ | 8 | 20 |
| Summertime Machine Oil | (commercially available) | 5 | 20 |
| Kelthane Emulsion | (commercially available) | 50 | 97 |

EXAMPLE 2

50 chemical-resistant female imagoes of *Panonychus citri* were inoculated on a Citrus unshiu sapling three years old. Then the sampling was allowed to stand in a large phytotron until five mites were observed on each leaf. 1000-fold and 1500-fold dilutions of Dani-cut Emulsion, Acar Emulsion and Omite Wettable Powder were prepared and the compounds (2) and (6) of the present invention were added to each dilution to give a concentration of 500 ppm, thus preparing a dilution mixture. 1000-fold and 1500-fold dilutions of Dani-cut Emulsion, Acar Emulsion and Omite Wettable Powder were employed as a control. 50 ml of dilution was applied to each sampling. After being allowed to stand for seven and 21 days, ten leaves per sampling were collected at random and the mites thereon were counted. The miticidal rate was represented based on the data obtained from the untreated lot. This procedure were repeated twice. Table 2 shows the result.

TABLE 2

| Lot | After treatment period (days) | Commercially available miticides | | | | | |
|---|---|---|---|---|---|---|---|
| | | Dani-cut Emulsion | | Acar Emulsion | | Omite Wettable Powder | |
| | | × 1000 | × 1500 | × 1000 | × 1500 | × 1000 | × 1500 |
| Compound (6) of invention (500 ppm) | 7 | 98 | 92 | 100 | 92 | 100 | 92 |
| | 21 | 96 | 84 | 100 | 81 | 100 | 81 |
| Compound (2) of invention (500 ppm) | 7 | 92 | 79 | 94 | 81 | 100 | 72 |
| | 21 | 78 | 62 | 54 | 32 | 68 | 45 |
| — | 7 | 72 | 42 | 50 | 29 | 54 | 29 |
| | 21 | 48 | 30 | 21 | 10 | 32 | 15 |

The above result suggests that the miticide of the present invention exhibits a remarkable effect on chemical-resistant mites when used together with commercially available miticides.

EXAMPLE 3

The chemical damage to crops caused by the compound of the present invention was examined as follows. 1000 ppm per pot of the compound of the present invention was applied on cucumber and soybean plants in the three- to four-foliate stage until each plant was sufficient moistened. Then the plant was allowed to stand in a green house. One and seven days after the treatment, the occurrence of chemical damage was examined with the naked eye.

For comparison, the comparison compound (1) and Summer Machine Oil (a commercially available product) were used at the same concentration as that of the compound of the invention. Table 3 shows the result.

TABLE 3

| Lot | Crop for examining chemical damage | |
|---|---|---|
| | Cucumber | Soybean |
| Compound (2) of the invention | no damage | no damage |
| Compound (6) of the invention | no damage | no damage |
| Comparison (1) | brown spots | brown spots |
| Summertime Machine Oil | no damage | brown spots |

What is claimed is:

1. A composition for use in the extermination of mites comprising a quaternary ammonium salt of the formula (I):

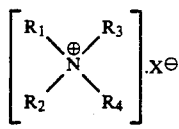

(I)

wherein $R_1$ and $R_2$ are independently selected from the group consisting of

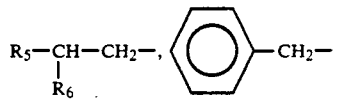

and an alkyl group having 1 to 4 carbon atoms, provided at least one of $R_1$ and $R_2$ is

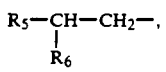

wherein $R_5$ is an alkyl or alkenyl group having 4 to 22 carbon atoms, and $R_6$ is an alkyl or alkenyl group having 2 to 20 carbon atoms; $R_3$ and $R_4$ are independently selected from the group consisting of an alkyl group having 1 to 4 carbon atoms and —$CH_2CH_2OH$; and $X^-$ represents a counter anion; in combination with another compound effective in killing mites, said quaternary ammonium salt being contained in said composition in an amount of 10–2000 ppm and at a ratio of 0.1/1 to 20/1 with respect to said compound effective in killing mites.

2. A composition as set forth in claim 1, which is in the form of an aqueous solution or an aqueous dispersion.

3. A composition as set forth in claim 1, wherein $X^-$ is selected from the group consisting of $Br^-$, $Cl^-$ and $CH_3SO_4^-$.

4. A composition as set forth in claim 1, wherein said quaternary ammonium salt is

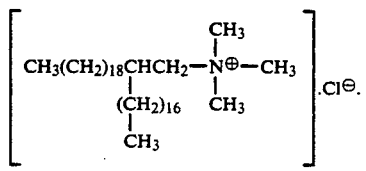

5. A composition as set forth in claim 1, wherein said quaternary ammonium salt is

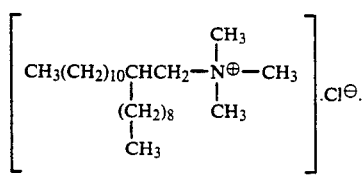

6. In a method of exterminating mites comprising the contacting of the mites with a composition effective to kill said mites, the improvement comprising said composition containing a quaternary ammonium salt of the formula (I):

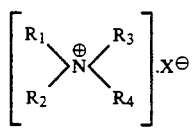

wherein $R_1$ and $R_2$ are independently selected from the group consisting of

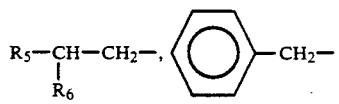

on all alkyl group having 1 to 4 carbon atoms, provided at least one of $R_1$ and $R_2$ is
wherein $R_5$ is an alkyl or alkenyl group having 4 to 22 carbon atoms, and $R_6$ is an alkyl or alkenyl group having 2 to 20 carbon atoms; $R_3$ and $R_4$ are independently selected from the group consisting of an alkyl group having 1 to 4 carbon atoms and $-CH_2CH_2OH$; and $X^{\ominus}$ represents a counter anion.

7. A method as claimed in claim 6, wherein said composition is in the form of an aqueous solution or an aqueous dispersion.

8. A method as claimed in claim 6, wherein $X^{\ominus}$ is selected from the group consisting of $Br^-$, $Cl^-$ and $CH_3SO_4^-$.

9. A method as claimed in claim 6, wherein said composition further contains another compound effective in killing mites, said quaternary ammonium salt being contained in said composition in an amount of 10–2000 ppm and a ratio of 0.1/1 to 20/1 with respect to said compound effective in killing mites.

10. A method as claimed in claim 6, wherein said quaternary ammonium salt is

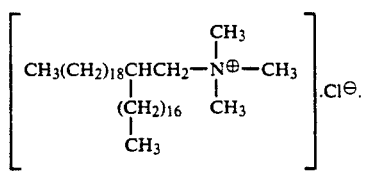

11. A method as claimed in claim 6, wherein said quaternary ammonium salt is

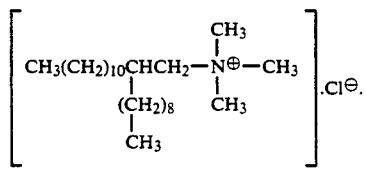

12. A method as claimed in claim 9, wherein said quaternary ammonium salt is

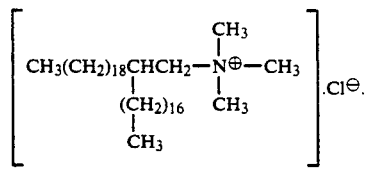

13. A method as claimed in claim 9, wherein said quaternary ammonium salt is

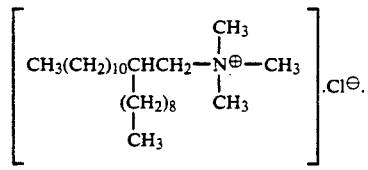

UNITED STATES PATENT AND TRADEMARK OFFICE
CERTIFICATE OF CORRECTION

PATENT NO. : 5,100,920

DATED : March 31, 1992

INVENTOR(S) : Tetsuji IWASAKI et al

It is certified that error appears in the above-identified patent and that said Letters Patent is hereby corrected as shown below:

Column 9, line 31, change "on all" to ---and an---.
　　　　　line 32; after "$R_2$ is" insert $$---R_5-\underset{\underset{R_6}{|}}{CH}-CH_2-, ---$$

Column 10, line 1; after "and" insert ---at---.

Signed and Sealed this

Twenty-fourth Day of August, 1993

Attest:

BRUCE LEHMAN

Attesting Officer　　　Commissioner of Patents and Trademarks